(12) United States Patent
Zhang et al.

(10) Patent No.: US 12,402,951 B2
(45) Date of Patent: Sep. 2, 2025

(54) METHOD FOR VISUALIZATION AND ORIENTATION GUIDANCE DURING ENDOSCOPY PROCEDURE

(71) Applicant: CANON U.S.A., INC., Melville, NY (US)

(72) Inventors: Hualei Shelley Zhang, Brookline, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 698 days.

(21) Appl. No.: 17/565,319

(22) Filed: Dec. 29, 2021

(65) Prior Publication Data
US 2022/0202502 A1 Jun. 30, 2022

Related U.S. Application Data

(60) Provisional application No. 63/132,320, filed on Dec. 30, 2020.

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00043* (2013.01); *A61B 1/00096* (2013.01);
(Continued)

(58) Field of Classification Search
CPC .......... G16H 15/00; G06N 3/02; G06N 20/00; G06T 7/0012; G06T 7/50; G06T 19/00; G06T 2207/10068; G06T 2207/10081; G06T 2207/30084; G06T 2210/41; A61B 1/00006; A61B 1/00009; A61B 1/000094; A61B 1/000095; A61B 1/0004; A61B 1/00043; A61B 1/0005; A61B 1/00052; A61B 1/00096; A61B 1/00097; A61B 1/00135; A61B 1/00174; A61B 1/00194; A61B 1/0052; A61B 1/0055; A61B 1/0057; A61B 1/01; A61B 1/2676; A61B 1/307;
(Continued)

(56) References Cited

U.S. PATENT DOCUMENTS 10,679,417 B2   6/2020   Wei et al.
2010/0249507 A1* 9/2010  Prisco .................. A61B 1/0002
                                              600/117

(Continued)

OTHER PUBLICATIONS

Zang X, Gibbs JD, Cheirsilp R, Byrnes PD, Toth J, Bascom R, Higgins WE. Optimal route planning for image-guided EBUS bronchoscopy. Comput Biol Med. Sep. 2019;112:103361.

*Primary Examiner* — Jacinta M Crawford
(74) *Attorney, Agent, or Firm* — Canon U.S.A., Inc., IP Division

(57) ABSTRACT

Apparatuses and methods for medical applications and, more particularly, to steerable flexible medical devices applicable to guide tools and devices in medical procedures, including endoscopes, cameras, and catheters are provided. The apparatuses and methods also include generating a panoramic image of an interior of a branching structure at or near the distal end of the flexible medical device wherein the panoramic image is generated based on the images of the branching structure.

23 Claims, 13 Drawing Sheets

(51) Int. Cl.
  *A61B 1/005* (2006.01)
  *A61B 34/10* (2016.01)
(52) U.S. Cl.
  CPC ........ *A61B 1/00174* (2013.01); *A61B 1/0057* (2013.01); *A61B 34/10* (2016.02); *A61B 2034/2051* (2016.02)
(58) Field of Classification Search
  CPC ......... A61B 5/061; A61B 18/26; A61B 34/10; A61B 34/20; A61B 34/30; A61B 34/35; A61B 34/74; A61B 90/36; A61B 90/361; A61B 2017/00323; A61B 2017/00809; A61B 2018/00511; A61B 2018/00904; A61B 2018/00982; A61B 2034/107; A61B 2034/2048; A61B 2034/2051; A61B 2034/258; A61B 2034/302; A61B 2034/306; A61B 2034/742; A61B 2090/306; A61B 2090/309; A61B 2090/364
  USPC ......................................................... 345/420
  See application file for complete search history.

(56) References Cited

U.S. PATENT DOCUMENTS

| | | | |
|---|---|---|---|
| 2017/0071456 A1* | 3/2017 | Ratnakar | ................. A61B 1/126 |
| 2019/0231220 A1* | 8/2019 | Refai | ................. A61B 1/00172 |
| 2020/0046208 A1* | 2/2020 | Kasai | ................. A61B 1/3132 |

* cited by examiner

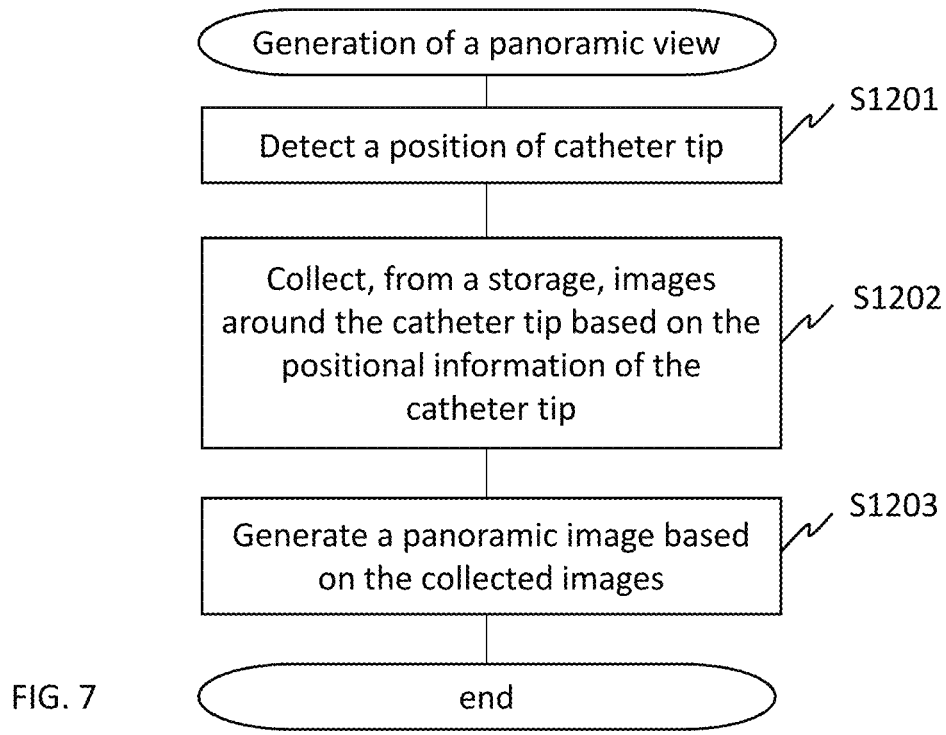

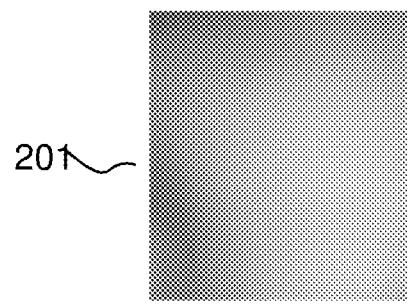
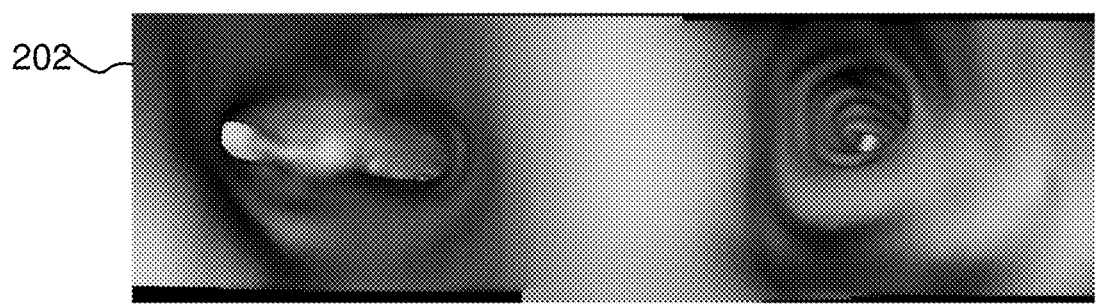
FIG. 9(A)
FIG. 9(B)
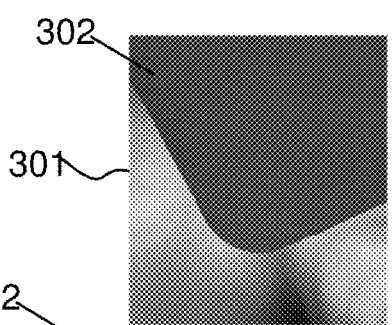
FIG. 10(A)
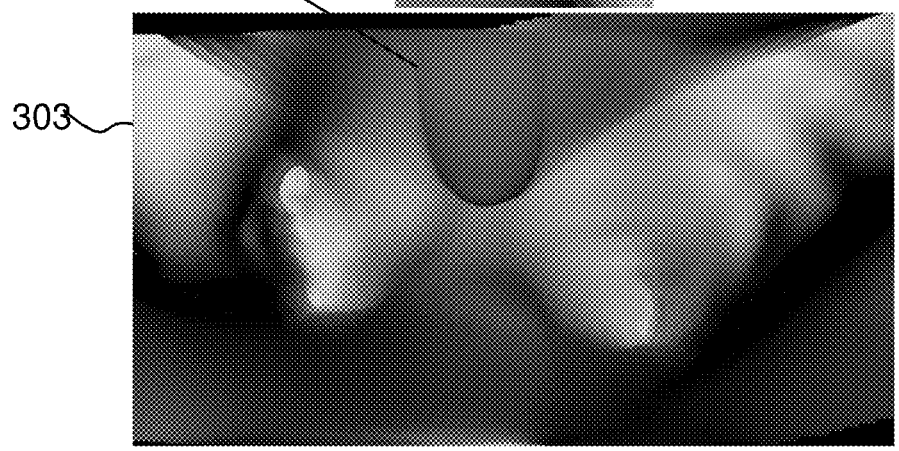
FIG. 10(B)

METHOD FOR VISUALIZATION AND ORIENTATION GUIDANCE DURING ENDOSCOPY PROCEDURE

CROSS-REFERENCE TO RELATED APPLICATIONS

The present application claims priority to U.S. provisional application 63/132,320 filed Dec. 30, 2020. The disclosure of the above-listed provisional application is hereby incorporated by reference in its entirety for all purposes. Priority benefit is claimed under 35 U.S.C. § 119(e).

BACKGROUND

Technical Field

This application generally concerns apparatuses and methods for medical applications and, more particularly, to steerable flexible medical devices applicable to guide tools and devices in medical procedures, including endoscopes, cameras, and catheters.

Background

Flexible medical instruments, which include endoscopic surgical instruments and catheters, are broadly used in surgical and probative settings. Flexible medical instruments generally include a flexible tube, commonly referred to as a sleeve or sheath, with one or more tool channels extending along (typically inside) the sheath to allow access to end effectors located at a distal end of the sheath.

SUMMARY

Some embodiments of a system comprise one or more memories and one or more processors in communication with the one or more memories. The one or more processors operate with the one or more memories to cause the system to perform operations that include obtaining a model of a branching structure; obtaining a position, relative to the branching structure, of a distal end of a flexible medical device; obtaining images of the branching structure, that are at or near the distal end of the flexible medical device; and generating a panoramic image of an interior of the branching structure at the position of the distal end of the flexible medical device, wherein the panoramic image is generated based on the images of the branching structure, that are at or near the distal end of the flexible medical device, and wherein a field of view of the panoramic image is greater than a field of view of a camera at the distal end of the flexible medical device.

Some embodiments of a method comprise obtaining a model of a branching structure; obtaining a position, relative to the branching structure, of a distal end of a flexible medical device; obtaining images of the branching structure, that are at or near the distal end of the flexible medical device; and generating a panoramic image of an interior of the branching structure at the position of the flexible medical device. The panoramic image is generated based on the images of the branching structure, which are at or near the distal end of the flexible medical device.

Some embodiments of one or more computer-readable media store instructions that, when executed by one or more computing devices, cause the one or more computing devices to perform operations that comprise obtaining a model of a branching structure; obtaining a position, relative to the branching structure, of a distal end of a flexible medical device; obtaining images of the branching structure, that are at or near the distal end of the flexible medical device; and generating a panoramic image of an interior of the branching structure at the position of the flexible medical device, wherein the panoramic image is generated based on the images of the branching structure, that are at or near the distal end of the flexible medical device.

Some embodiments of a system comprise one or more memories and one or more processors in communication with the one or more memories. The one or more processors operate with the one or more memories to cause the system to perform operations that include obtaining a model of a branching structure; obtaining a position, relative to the branching structure, of a tracking sensor embedded at distal end of a flexible medical device; and synthesizing a panoramic view image by combining multiple view-angle images of an interior space of the model of the branching structure, based at a selectable distal position of the flexible medical device.

Some embodiments of a system comprise one or more memories and one or more processors in communication with the one or more memories. The one or more processors operate with the one or more memories to cause the system to perform operations that include obtaining a route through a branching structure; obtaining a position, relative to the branching structure, of a distal end of a flexible medical device; obtaining an orientation of the distal end of the flexible medical device; calculating a guidance direction based on the route, on the position of the distal end, and on the orientation of the distal end; and adding a guidance indicator, that indicates the guidance direction, to, for example, the next branch in the branching structure along a planned navigation route or of preference by the operator.

Some embodiments of a system comprise one or more memories and one or more processors in communication with the one or more memories. The one or more processors operate with the one or more memories to cause the system to perform operations that include generating an image of an interior of a branching structure at a position of a distal end of a flexible medical device; receiving an indication of an orientation in the image of the interior of the branching structure, and controlling the flexible medical device to orient the distal end of the flexible medical device to the orientation.

BRIEF DESCRIPTION OF THE DRAWINGS

Further objectives, features and advantages of the present disclosure will become apparent from the following detailed description when taken in conjunction with the accompanying figures showing illustrative embodiments of the present disclosure.

FIG. 7 illustrates an example embodiment of an operational flow for synthesizing panoramic images.

FIG. 8 illustrates an example embodiment of an operational flow for maneuvering the tip of the catheter device and generating panoramic images.

FIGS. 9(A) and 9(B) illustrate an example embodiment of a panoramic image at the tip of the catheter device.

FIGS. 10(A) and 10(B) illustrate illustrates an example embodiment of a panoramic image at a proximal distance from the tip of the catheter device.

DESCRIPTION

The following paragraphs describe certain explanatory embodiments. Other embodiments may include alternatives, equivalents, and modifications. Additionally, the explanatory embodiments may include several features, and a particular feature may not be essential to some embodiments of the devices, systems, and methods that are described herein.

As used herein, the conjunction "or" generally refers to an inclusive "or," though "or" may refer to an exclusive "or" if expressly indicated or if the context indicates that the "or" must be an exclusive "or."

Figure 1:
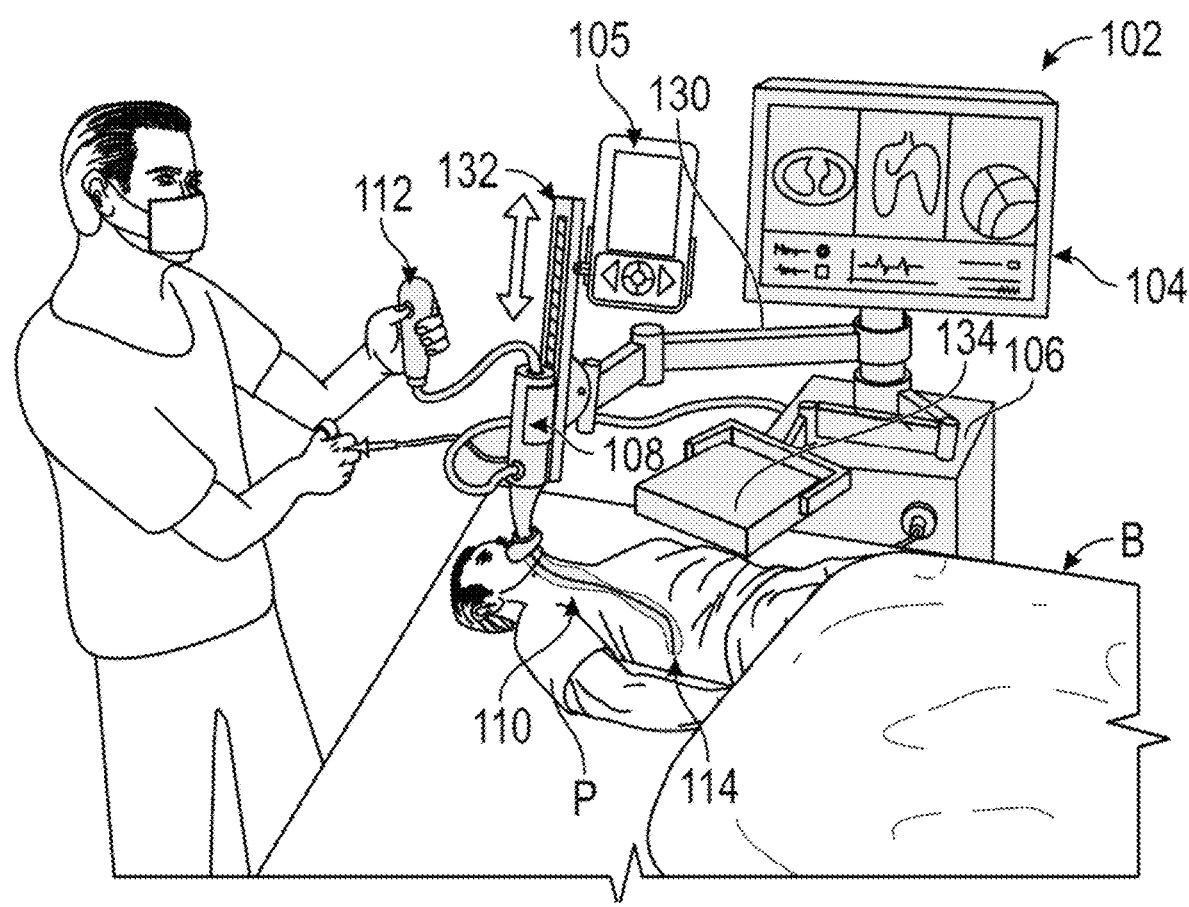
FIGS. 1 and 2 illustrate an example embodiment of an endoscope system.
Figure 2:
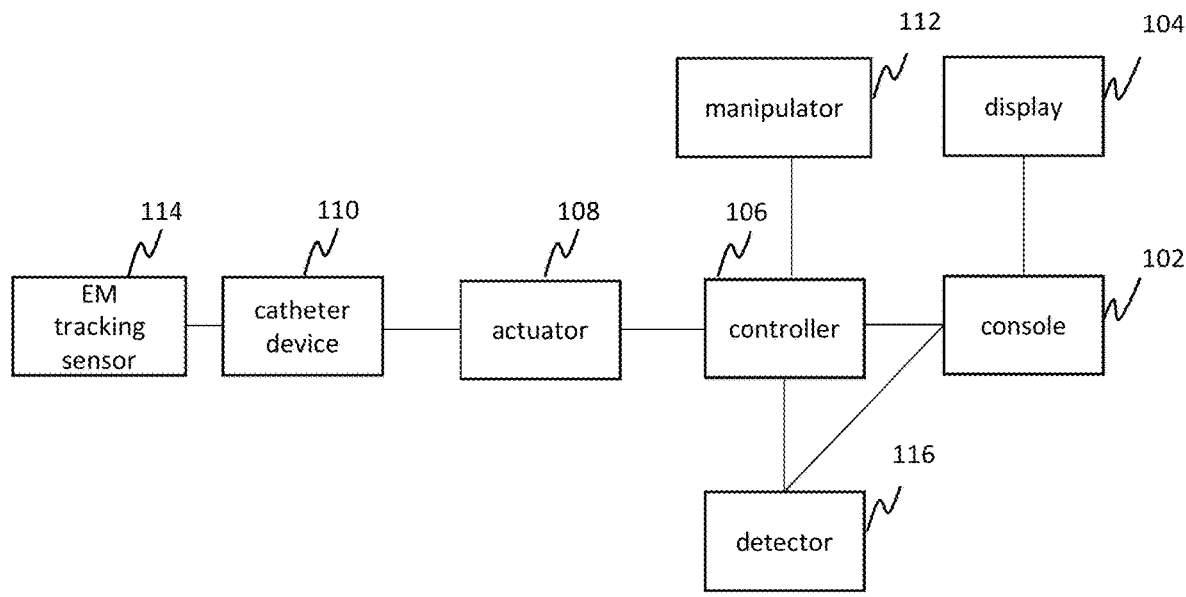

FIGS. 1 and 2 illustrate an example embodiment of an endoscope system. The system includes a console 102, a display 104, a controller 106, an actuator 108, a flexible medical device 110 (e.g., a catheter (the example used in the drawings), an endoscope), a manipulator 112, a tracking sensor 114 (e.g., an electromagnetic (EM) tracking sensor), a detector 116, and a camera 118. The controller 106 and the console 102 can be configured as separate devices. Alternatively, the controller 106 and the console 102 can be configured as one device. The display 104 may contain only the main display screen (also 104) are may also or alternatively contain a second display screen 105 or configured to provide a user with a graphical user interface (GUI) for interacting with and controlling the flexible medical device 110.

As depicted in use, a patient (P) disposed on a bed (B), in a supine position, is the subject of an endoscopic interventional procedure. The flexible medical device 110 may be held by a robotic system including a first robot arm 130 includes one or more actuated arm links configured to hold and position a linear stage 132 aligned with respect to the patient P. Other components that may be part of the endoscope system as described herein include a support platform for the actuator 108. An additional handle may be used to control the flexible medical device 110. A holder such as an actuated arm can be used to hold and position an electromagnetic field generator 134 in embodiments where the tracking sensor 114 is an electromagnetic sensor. The EM field generator is used in conjunction with the EM sensor 114 to generate an EM tracking signal used as described herein as well as for registration and/or navigation.

The console 102 executes software and controls the display 104 to display a navigation screen. The console 102 may generate one or more three-dimensional (3D) models of an internal branching structure (e.g., lungs, blood vessels) of a patient based on medical images, such as computed tomography (CT) images and magnetic resonance imaging (MRI) images. Also, 3D models may be received by the console 102 from other devices. The display 104 may be attached to the console 102 or be a separate or dual display elsewhere in the operating theatre.

The console 102 acquires catheter-position information from the controller 106, which acquires the catheter-position information from the detector 116. Additionally, the console 102 may acquire the catheter-position information directly from the detector 116.

By executing the software, the console 102 generates and outputs a navigation screen to the display 104, and the navigation screen is based on the 3D model and the catheter-position information. The navigation screen indicates a current position of the flexible medical device 110 in relation to the 3D branching model. Thus, a user can recognize the current position of the flexible medical device 110 in the branching structure.

The endoscope system may be used for medical procedures and may be configured along with other components including a computer cart enclosing a computer system. The endoscope system may be attached to a support platform such as one having a robotic arm and/or a linear stage for movement of the flexible medical device 110.

The endoscope system can be configured to perform an endoscopy procedure on a patient which is disposed on a medical table or bed. To that end, a user may perform a manual insertion mode and insert the flexible medical device 110 to a predetermined location of the patient's anatomy (e.g., the user may perform manual insertion of a bronchoscope to the first carina of a patient), while observing the insertion on the display 104. A separate mode for the endoscope system is robot mode, where the controller 106 kinematically controls the actuators 108 or motors to bend, twist or rotate the probe via one or more control wires within the flexible medical device 110. The actuator 108 includes one or more motors and drives each section of the flexible medical device by pushing and/or pulling the driving wires.

Figure 3:
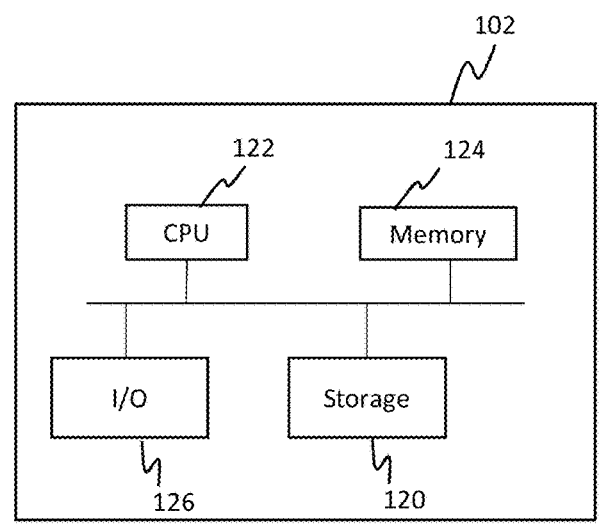
FIG. 3 illustrates an example embodiment of a console.

FIG. 3 illustrates an example embodiment of a console. The console 102 includes at least one storage 120, at least one processor 122, at least one memory 124, and one or more I/O components 126.

The storage 120 stores the software. And some embodiments of the storage 120 include one or more of the following: a magnetic disk (e.g., a floppy disk, a hard disk), an optical disc (e.g., a CD, a DVD, and a Blu-ray), a magneto-optical disk, magnetic tape, and semiconductor memory (e.g., a solid-state drive). The memory 124 is used as a work memory. And some embodiments of the memory 124 include one or more of the following: flash memory, SRAM, and DRAM.

The one or more processors 122 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The one or more processors 122 execute the software developed in the memory 124.

The I/O components 126 include communication components (e.g., a GPU, a network-interface controller) that communicate with the display 104, the detector 116, and other input or output devices (not illustrated), which may include a keyboard, a mouse, a printing device, a touch screen, a light pen, an optical-storage device, a scanner, a microphone, and other computing devices. The I/O components 126 input the catheter-position information to the console 102 and output information for displaying the navigation screen to the display 104.

Figure 4:
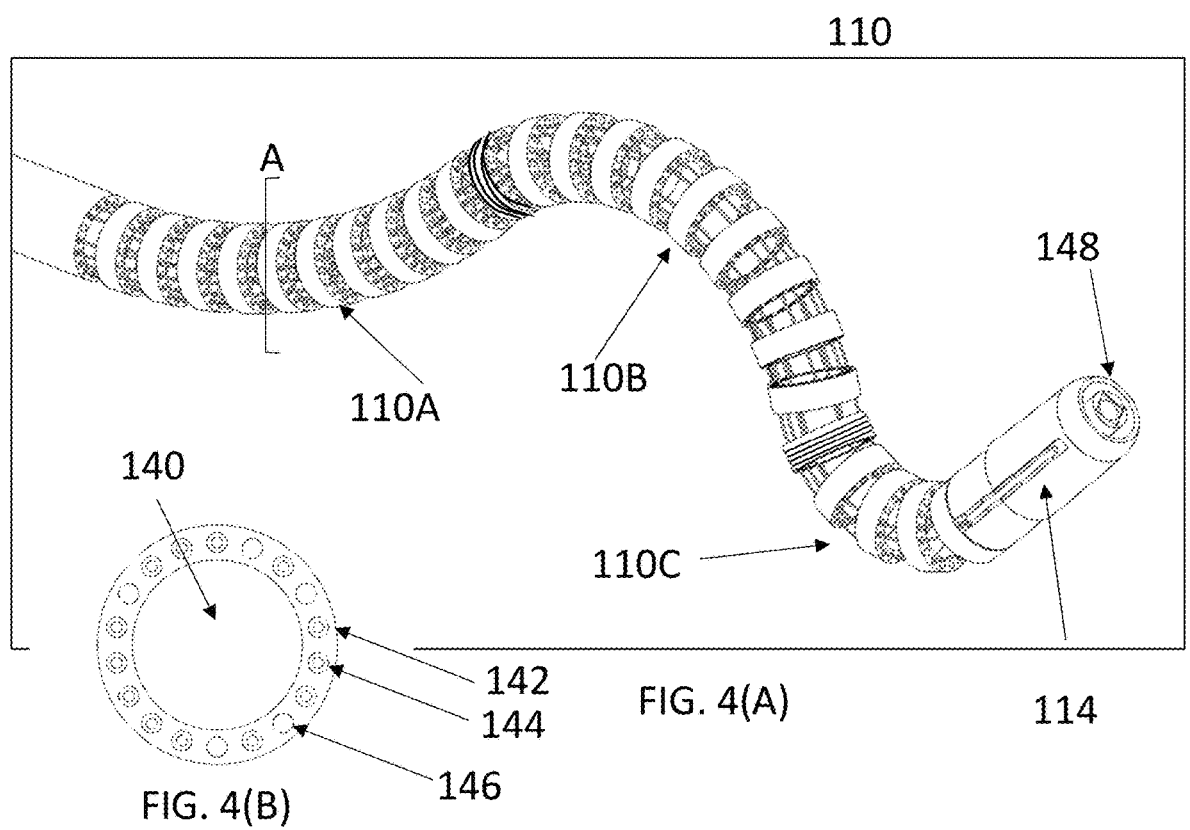
FIGS. 4(A) and 4(B) illustrates an example embodiment of a flexible medical device.

FIG. 4(A) illustrates an example embodiment of a flexible medical device 110. The flexible medical device 110 includes a proximal section 110A, a middle section 110B, and a distal section 110C. Running proximal to distal through the device is a hollow chamber 140 that may be used as a working channel for medical procedures. Each section is bent by a plurality of driving wires 142 (driving liner members) as driving backbones. The posture of the flexible medical device is supported by supporting wires 144 (supporting liner members) as passive sliding backbones. The driving wires 142 and supporting wires 144 are located in lumen 146 surround the central hollow chamber 140 as shown in the cross-sectional view of FIG. 4(B). One or more lumen 146 may be left free to facilitate the use of additional optical fibers or wires to be added to the device. A tracking sensor 114 is attached to the atraumatic tip 148 of the flexible medical device 110. At the proximal end of the flexible medical device 110, the driving wires are connected to the actuator 108, as indicated in FIG. 2 above where the detector 116 can detect a position of the tracking sensor 114 and output the detected positional information to the controller 106 or the console 102.

In some embodiments, the flexible medical device 110 is an endoscope. As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

The controller 106 receives the positional information of the flexible medical device tip from the detector 116. And the controller 106 controls the actuator 108 in accordance with the manipulation by a user via one or more manipulators 112. The controller 106 may control the flexible medical device 110 based on an algorithm, such as a follow-the-leader (FTL) algorithm. By applying the FTL algorithm, the middle and proximal sections of the flexible medical device 110 move at a first position in the same way that the distal section moves at the first position or a second position next to the first position.

During an image-guided biopsy procedure, the flexible medical device 110 navigates through branching structures inside a patient's body. Medical images (e.g., a medical image volume), such as CT images and MRI images, can be acquired in advance or in real-time, and a branching model can be generated from the images to provide guidance during the procedure. The position of the tip of the flexible medical device 110 can be detected by the detector 116, which is provided outside of the patient's body and which can detect the tracking sensor 114 at the tip of the flexible medical device 110.

After successful registration of the image space and the flexible-medical-device space, the flexible medical device 110 is continuously or continually located relative to the three-dimensional branching model, which provides meaningful guidance to a user. In conjunction, the user often uses camera vision, from the camera 118 located at the front of the flexible medical device's tip, to obtain information such as a forward-facing view of the surroundings inside the patient's body.

During procedure, the flexible medical device 110 navigates inside the branching structure under the guidance of three-dimensional branching model extracted from the medical images. When the flexible medical device 110 is near splitting junctions or within a narrow peripheral branch, where the flexible medical device 110 is in a constricted space or in tight interface with the interior sidewall of the branching structure, the user may lose sight of the lumen and the direction towards the target of the biopsy. It may become difficult to quickly maneuver the flexible medical device 110 when the flexible medical device's tip is obstructed by the interior sidewall inside narrow branches, for example branches towards the periphery of the branching structure. As an example, a camera view that looks forward with an angle of view of less than 60° may not be effective for navigation or visualization if the tip is angled away from the splitting junction.

The console is configured to generate panoramic images that show panoramic views of the interior of the branching structure. The panoramic images may be stitched from synthesized images of multiple view angles, which are images that are generated based on the catheter device and its relation with the three-dimensional (3D) model of the branching structure. And the panoramic images may be stitched from physically captured images by one or more cameras 118 when turning the tip of a flexible medical device. In some embodiments, the panoramic images may be generated by a combination/stitching of synthesized and camera captured images. For example, if the camera's range of movement is limited to less than the desired range of the panoramic view (e.g., because the camera's range of movement is blocked by an interior wall or because the endoscope is significantly angled and has a reduced range of motion in the desired direction), for a static case the camera can have a horizontal field of view of 90°, the part of the panoramic image that is within the camera's range of movement can be generated by camera capture with catheter tip turning, and the rest of the panoramic image can be generated by synthesizing, i.e. 45° on each peripheral side.

Thus, in some embodiments, the view angle of the panoramic view image spans at least −45° to +45°. In other embodiments, a larger view is preferred, and the view angle of the panoramic view image spans at least −60° to +60°. In yet other embodiments the view angle of the panoramic view image spans at least −90° to +90°. The panoramic view image may have a fisheye effect in some embodiments.

Accordingly, the console can generate panoramic images that show various panoramic views. The console may allow a user to select one or more axes of rotation that are used to generate the panoramic image. And the console may allow the user to select the viewpoint of the panoramic image. For example, the viewpoint may be the front of the flexible medical device's tip, or the viewpoint may be a location proximal from the flexible medical device's tip.

In some embodiments, the field of view of the panoramic image is greater than a field of view of a camera at the distal end of the flexible medical device. In some embodiments, the field of view of the panoramic image is designed to have a span of rotation angles relative to the tip of the medical device that is different (e.g., 15°, 30°, 45° or more) from the angle provided by the camera.

Figure 5:
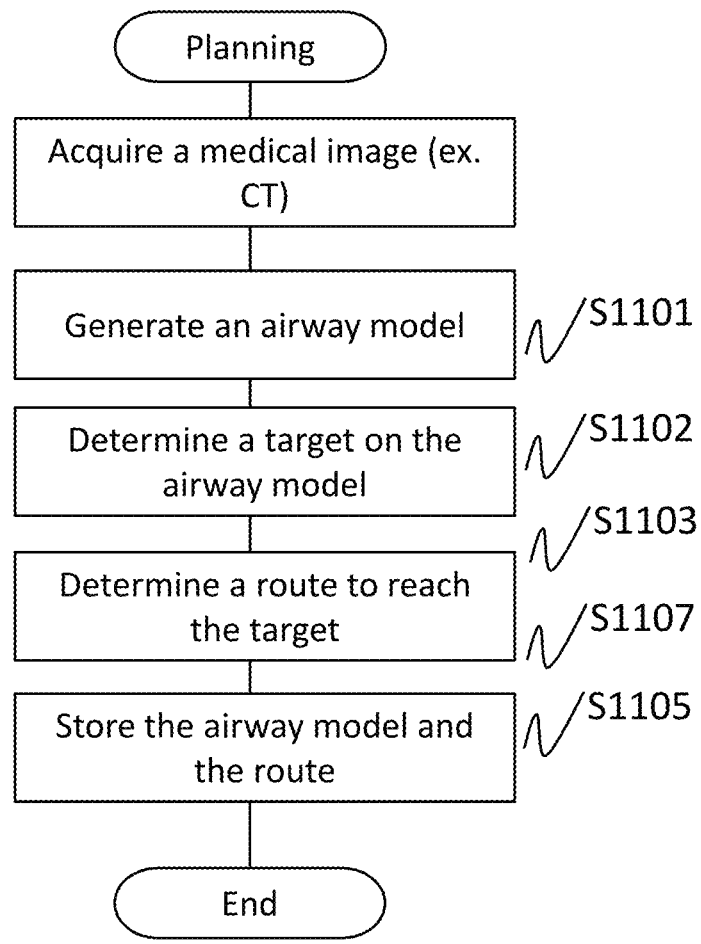
FIG. 5 illustrates an example embodiment of an operational flow for planning an endoscope procedure.

FIG. 5 illustrates an example embodiment of an operational flow for planning a procedure. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks.

Furthermore, although the operations in this operational flow and some of the operations in the other operational flows that are described herein are performed by a console, in some embodiments these operations are performed by two or more consoles or by one or more other specially-configured computing devices.

In S1101, the console acquires medical images, such as CT images and MRI images. The medical images may define an image stack (e.g., image volume). Next, in S1102, the console generates a 3D model of a branching structure (e.g., an airway model of a patient's lungs) based on the medical images. Then, in S1103, the console determines a target (e.g., biopsy target) based on the medical images and a user instruction.

In S1104, the console determines a route, through the 3D model, that the flexible medical device can follow to reach the target. Then, in S1105, the console stores the 3D model and the route (e.g., in the storage 120, in the memory 124).

Accordingly, in FIG. 5, a 3D model of a branching structure is generated, and a target and a route though the 3D model are determined and stored. And the operations in FIG. 5 can be performed before a flexible-medical-device operation is started.

Figure 6:
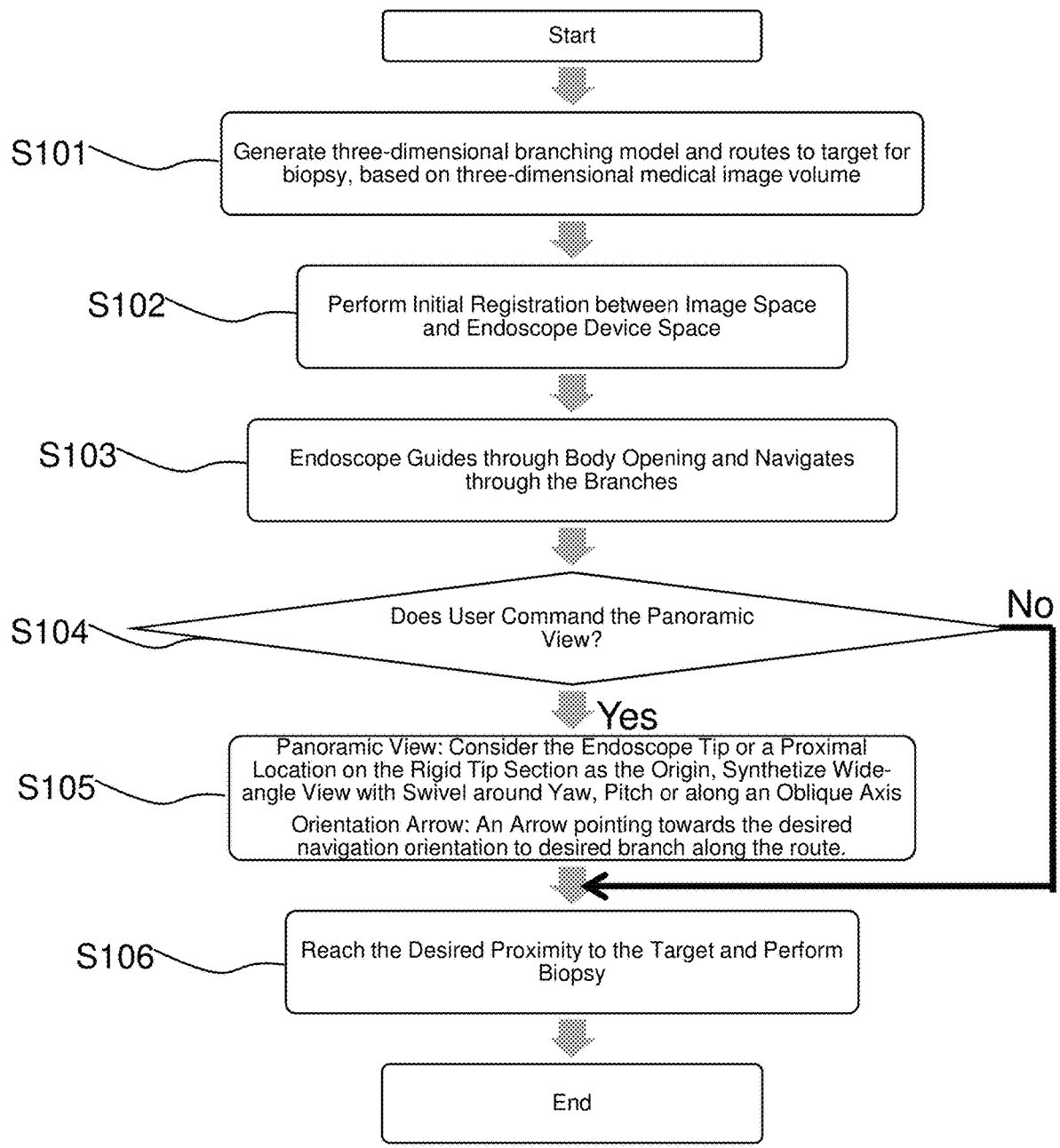
FIG. 6 illustrates an example embodiment of an operational flow for generating panoramic images during navigation phase of an endoscope procedure.

FIG. 6 illustrates an example embodiment of an operational flow for generating panoramic images during an endoscope navigation procedure. First, in S101, a console generates or obtains (e.g., from another computing device) a 3D branching model and one or more routes to a target, on the basis of medical images representing a branching structure. In S101, some embodiments of the console perform the operations that are described in FIG. 5.

Next, in S102, the console performs registration or alignment to merge the image space and the flexible-medical-device space in order to track the position of the flexible medical device's tip in relation to the branching model. After the registration of the flexible-medical-device space and the image space, the location of the flexible medical device's tip with respect to the branching model can be identified.

Then, in S103, the flexible medical device is guided into the branching structure in the patient body and starts to navigate throughout the branching structure.

In S104, in response to a user input (e.g., a trigger), the console device generates a panoramic view (e.g., synthetic panoramic view) from a viewpoint at or near the flexible medical device's tip and presents the panoramic view on the display. The user input may be an instruction to display the panoramic view around the flexible medical device's tip, and the user may provide the instruction via an input device (e.g., button, keyboard, or trigger). The panoramic view is generated based on the plurality of images near (e.g., around) the position of the flexible medical device's tip. The panoramic view may swivel around yaw, pitch, or a selected oblique axis, through a set rotation span (e.g., from −90 to +90 degrees, from −180 to +180 degrees). And the panoramic view may include a translation of the viewpoint, in addition to or in alternative to, the swiveling. The panoramic view may be displayed instead of a currently captured image (by the camera at the distal end of the flexible medical device) in response to receiving the user input. Alternatively, the panoramic view may be displayed in addition to the currently captured image in response to receiving the user input.

Finally, in S106, the flexible medical device is maneuvered to reach the target tissue and perform a biopsy or other operation. Alternatively, the instruction may be made automatically in accordance with a detection of the obstructed view based on images captured by a camera (e.g., endoscope) installed in the flexible medical device 110.

FIG. 7 illustrates an example embodiment of an operational flow for generating panoramic images. In this operational flow, the panoramic view is generated using a medical image volume that includes images that have already been captured and stored, for example in the storage 120. The medical images may be used to generate the 3D model as well as the panoramic view.

In S1201, the console acquires, from a detector 116, positional information that indicates a current position of a flexible medical device's tip. Next, in S1202, the console device collects, from the image volume (which, for example, may be stored in the storage 120 or in the memory 124), images around the flexible medical device's tip based on the positional information and on the 3D model. Then, in S1203, the console generates the panoramic view based on the images collected in S1202. For example, the panoramic view may be generated by stitching the collected images.

FIG. 8 illustrates an example embodiment of an operational flow for capturing panoramic images. In this embodiment, the panoramic view is generated based on images captured by a camera that is located at or near the tip of the flexible medical device 110 (e.g., the camera 118 in FIG. 2). In some embodiments, it is preferred that the camera is flush with the tip since a camera positioned in from the tip would have a field of view that is at least partially blocked by the catheter sheath.

Figure 16A:
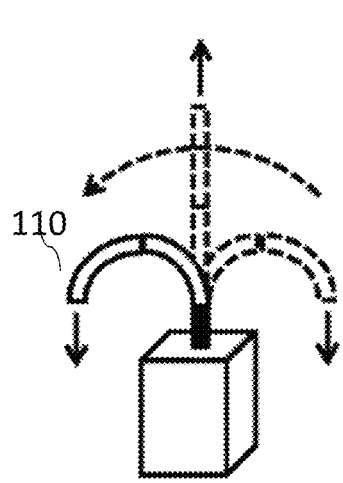
FIGS. 16(A)-16(C) illustrate movement patterns of a tip of a flexible medical device.
Figure 16B:
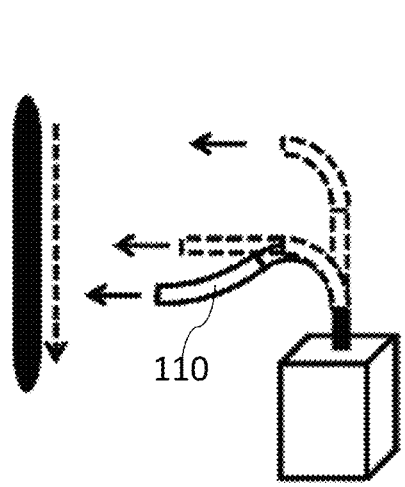
Figure 16C:
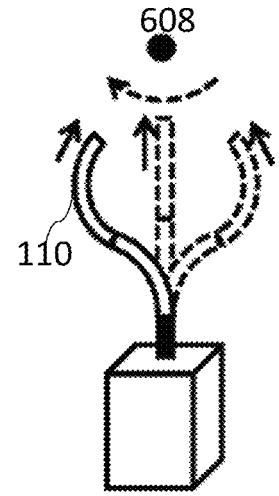

In S1301, console controls the flexible medical device to swivel the camera (e.g., the camera itself, the camera with the flexible-medical-device's tip) in accordance with an instruction to display the panoramic view around the flexible-medical-device's tip. The console can control the flexible medical device to swivel the camera around yaw, pitch, or a selected oblique axis, with a desired rotation span (e.g., −90 to +90 degrees, −180 to +180 degrees), and capture a plurality of images. Also, the console can control the flexible medical device to move the camera in a translation, either in addition to, or in alternative to, the swiveling. FIGS. 16A-C illustrate various movement modes of a tip (which may embed a camera) of a flexible medical device, 16A being bending movement, 16B being angled view movement, and 16C being remote-center or pivoting movement.

Next, in S1302, the console generates the panoramic view based on the images that were capture in S1301. For example, the console may stitch the images captured in S1301 to create the panoramic image.

Examples of panoramic views are illustrated in FIGS. 9, 10, 11A, and 11B.

FIGS. 9(A) and 9(B) illustrate an example embodiment of a panoramic image. When the camera 118 (not shown) faces the obstructed view of the interior sidewall, as shown in the image of FIG. 9(A), as image 201, navigation of the flexible medical device may be hindered. In FIG. 9(B), the panoramic image 202 displays a panoramic view in front of the flexible medical device's tip. In this embodiment, the panoramic view swivels around the yaw axis, with a rotation span of −90 to +90 degrees, to provide a broader view of the interior sidewall. A panoramic view that based on the view point at the tip of the flexible medical device (e.g., that swivels about the yaw axis) is at the distal end of the medical device and may be referred to herein as a "horse view."

FIGS. 10(A) and 10(B) illustrate illustrates another example embodiment of a panoramic image. When the camera 118 (not shown) faces the obstructed view of the interior sidewall, as shown in image of FIG. 10(A), as image 301, where an obstruction (the tip of the flexible medical device's tip 302) is shown navigation of the flexible medical device may be hindered. In FIG. 10(B), the panoramic image 303 in this embodiment displays a panoramic view at a proximal location from the flexible medical device's tip, which includes the flexible medical device's tip 302 as part of the field of view (this may be referred to herein as the "rider-view"). This view is located near the distal end of the medical device and at a position that is proximal from the distal tip of the medical device. It is not specifically at the tip of the medical device (at tip of the distal end) as in the "horse-view". In this view, the view is located a distance from the distal tip that is approximately the length of an atraumatic tip. In other similar views, the view may be located a distance from the distal tip that includes the length of the atraumatic tip and/or an additional proximal distance, setting the "rider" further back from the tip of the medical device. In FIG. 10(B), the panoramic image 303 was generated by swiveling around the yaw axis, with a rotation span of −90 to +90 degrees.

Figure 11A:
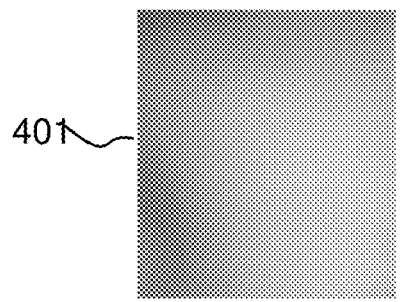
FIGS. 11(A)-11(D) illustrate an example embodiment of a panoramic image in fisheye effect. The image is at tip of the catheter device FIGS. 11(A) and 11(B) and a proximal distance from the tip of the catheter device (FIGS. 11(C)-11(D).
Figure 11B:
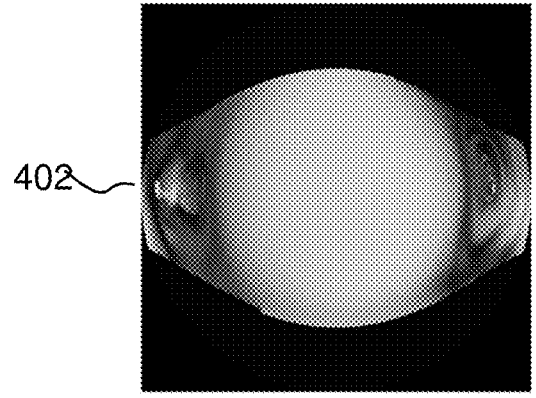

FIGS. 11(A) and 11(B) illustrate an example embodiment of a panoramic image. When the camera 118 faces the obstructed view of the interior sidewall, as shown in FIG. 11(A) as image 401, navigation of the flexible medical device may be hindered. The panoramic image 402 shown in FIG. 11(B) displays a panoramic view from a viewpoint at the front of the flexible medical device's tip. In this embodiment, the panoramic image 402 shows a panoramic view that has been distorted using barrel distortion (an ultra-wide-angle warping effect). Such a panoramic view may also be referred to herein as a "fisheye view." The panoramic image 402 in FIG. 11(B) warps the wide-angle view, swiveling around all directions within the plane perpendicular to the flexible medical device's tip, with a rotation span from −90 to +90 degrees.

Figure 11C:
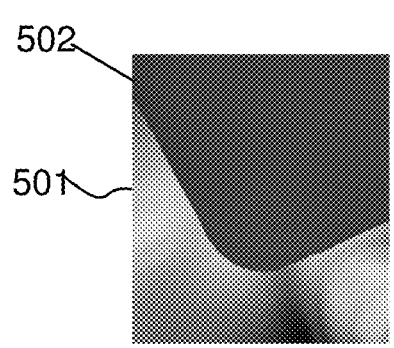
Figure 11D:
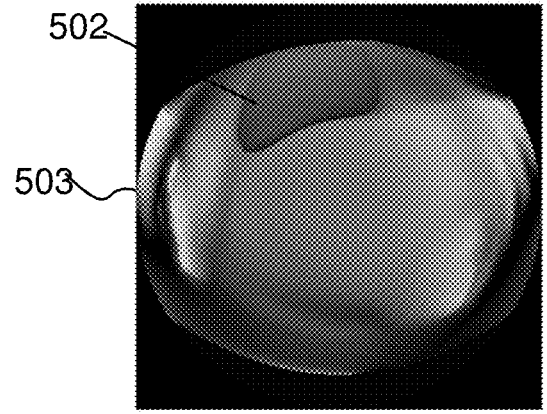

FIGS. 11(C) and 11(D) illustrate an example embodiment of a panoramic image. When the camera 118 faces the obstructed view of the interior sidewall, as shown in FIG. 11(C) as image 501, navigation of the flexible medical device may be hindered by the flexible medical device's tip 502. The panoramic image 503 shown in FIG. 11(D) displays a panoramic view from a viewpoint at a distance proximal to the flexible medical device's tip. In this embodiment, the panoramic image 503 shows a "fisheye view" that warps the wide-angle view, swiveling around all directions within the plane perpendicular to the flexible medical device's tip, with a rotation span from −90 to +90 degrees. The panoramic image also shows a "rider view," and thus includes the flexible medical device's tip 502 since the view is near but not at the distal end of the medical device. Note that the panoramic image 503 shows both effects of "fisheye view" and a "rider view."

Figure 12:
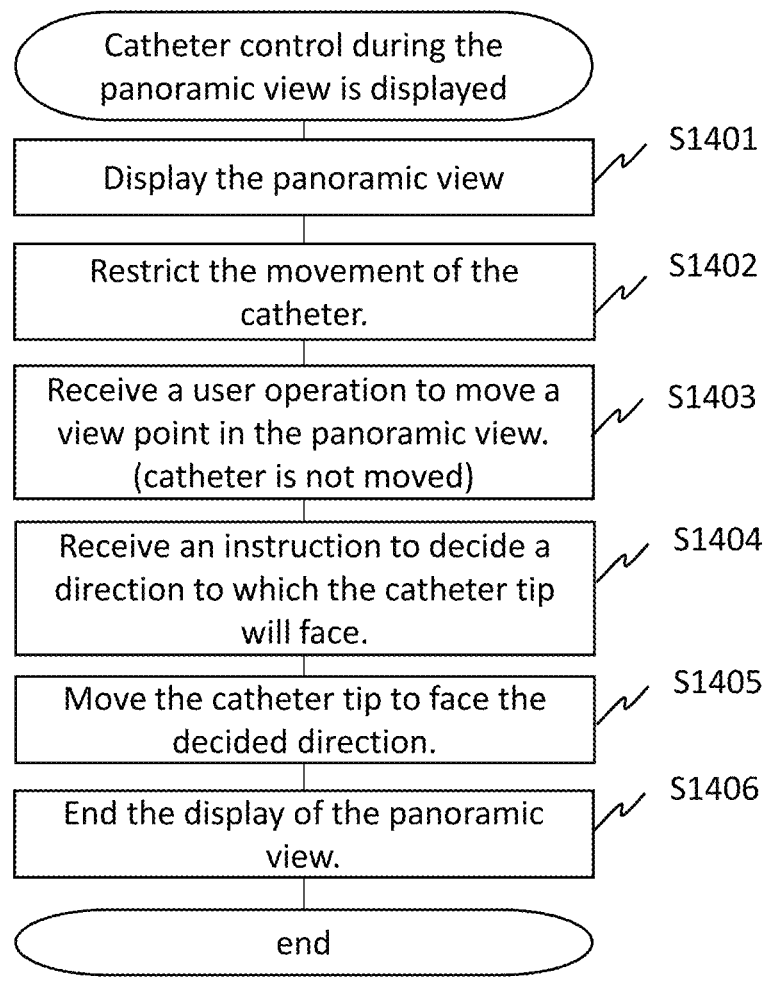
FIG. 12 illustrates an example embodiment of an operational flow for synthesizing panoramic images and generating direction indicator for visualization guidance.

FIG. 12 illustrates an example embodiment of an operational flow for displaying panoramic images. As described in FIG. 12, the movement of the flexible medical device can be restricted when the panoramic image is displayed and a user is checking the panoramic image. Also, before S1401, the console generates a panoramic image (e.g., according to FIG. 7, according to FIG. 8).

In S1401, the console presents the panoramic image on a display. For example, the consoled may present the panoramic image on the display according to a received instruction (e.g., an instruction received from a user). Next, in S1402, the console restricts the movement of the flexible medical device. When the movement of the flexible medical device is restricted, the flexible medical device does not move, even if a user inputs an instruction to change the view point in the panoramic view.

Then, in S1403, the console receives a user operation to move a view point in the panoramic image. For example, a user may operate the manipulator 112 (e.g., joystick) to change the view point in the panoramic image as if the user is controlling a movement of the flexible medical device's tip using the manipulator, although the flexible medical device (including the tip) does not move actually while the flexible medical device's movement is restricted (e.g., while the panoramic image is displayed). The way of a first operation of the manipulator 112 to change the view point in the panoramic view and of a second operation of the manipulator 112 to move the flexible medical device's tip when the panoramic view is not displayed may be the same. Thus, the same signal from the manipulator 112 (in response to the same input from a user) may cause the system to (1) change the view point in the panoramic image, without changing a position of the flexible medical device, when the panoramic image is displayed and (2) change a position of the flexible medical device when the panoramic image is not displayed.

Next, in S1404, the console receives an instruction that indicates, in the panoramic image, a direction in which the flexible medical device's tip will face (point in). Once the console receives the direction, the restriction of the movement of the flexible medical device is canceled.

In S1405, console controls the flexible medical device to move the tip to face (point in) the direction. Finally, in S1406, console ends the display of the panoramic image.

Thus, some embodiments of the guidance system (e.g., some embodiments of the console) allow a user to check the view around the flexible medical device's tip without moving the flexible medical device, and allow the user to use the same controls to change the view point of the panoramic image without moving the flexible medical device.

Figure 13A:
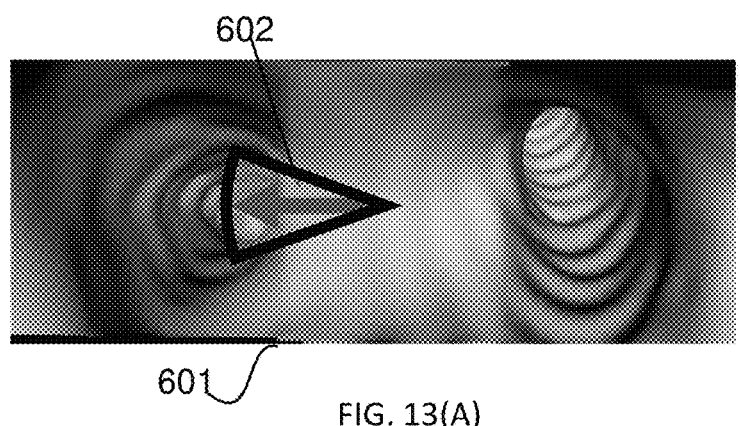
FIG. 13(A) illustrates an example embodiment of a panoramic image that includes direction indicator.

FIG. 13(A) illustrates an example embodiment of a panoramic image that includes guidance. In this embodiment, the guidance in the panoramic image 601 is shown as both an arrow and a fan shape 602 that is overlaid on the panoramic image 601. The console can compute and show the arrow 602 to point towards the next branch in the branching structure along a planned navigation route or according to a user's preference. Alternatively or in addition (as shown), a fan shape or similar indicator can show a range bounded by two limits, such that, as long as the direction is along the orientation within the fan shape, the movement will be towards the next branch in the branching structure.

Figure 13B:
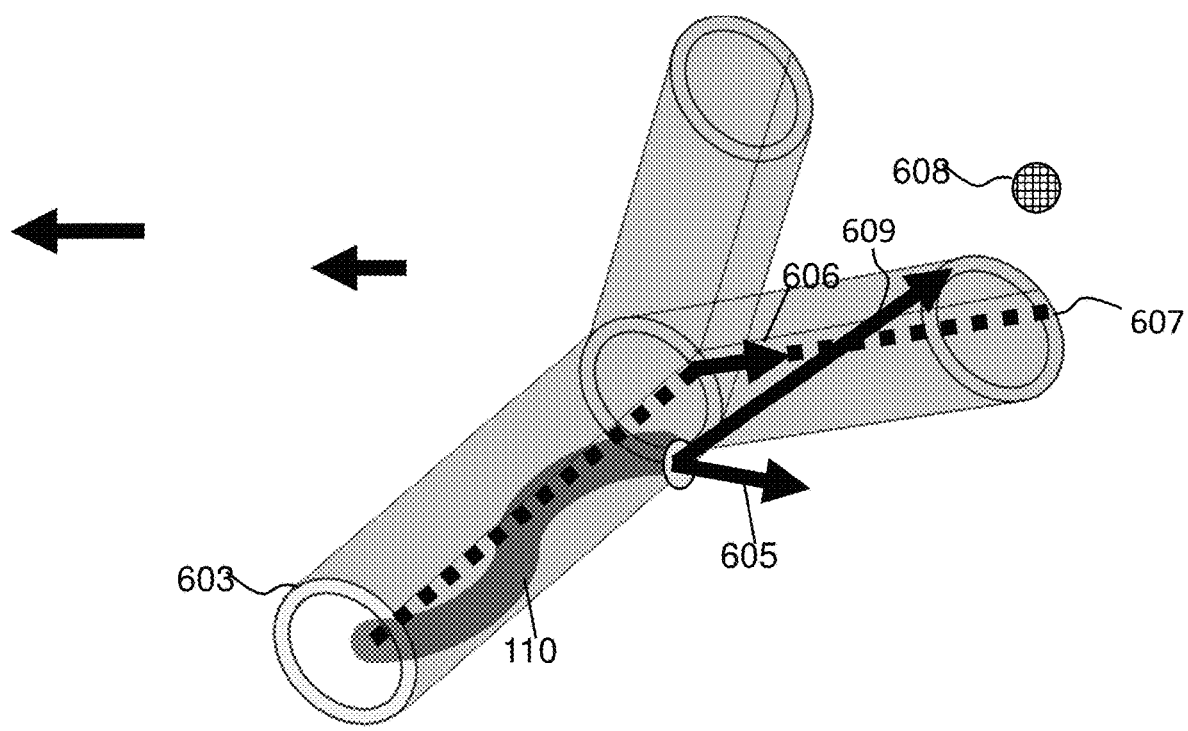
FIG. 13(B) illustrates an example embodiment of computing the indicator orientation for the catheter device in relation to the branching model.

FIG. 13(B) illustrates an example embodiment of the generation of guidance in a branching structure 603. FIG.

13(B) includes part of a planned route 607 to a target 608 through the branching structure 603. In this example, the tip of the flexible medical device 110 faces the interior sidewall of the branching structure 603 (as indicated by the orientation vector 605 from the flexible medical device's tip). The desired turning angle can be computed based on the dot product of the orientation vector 605 and the orientation vector 606 of the next sub-branch to navigate into. The sub-branch can be determined from next branch along the planned route 607 or the orientation vector 609 from the flexible medical device's tip towards the target 608.

Figure 14:
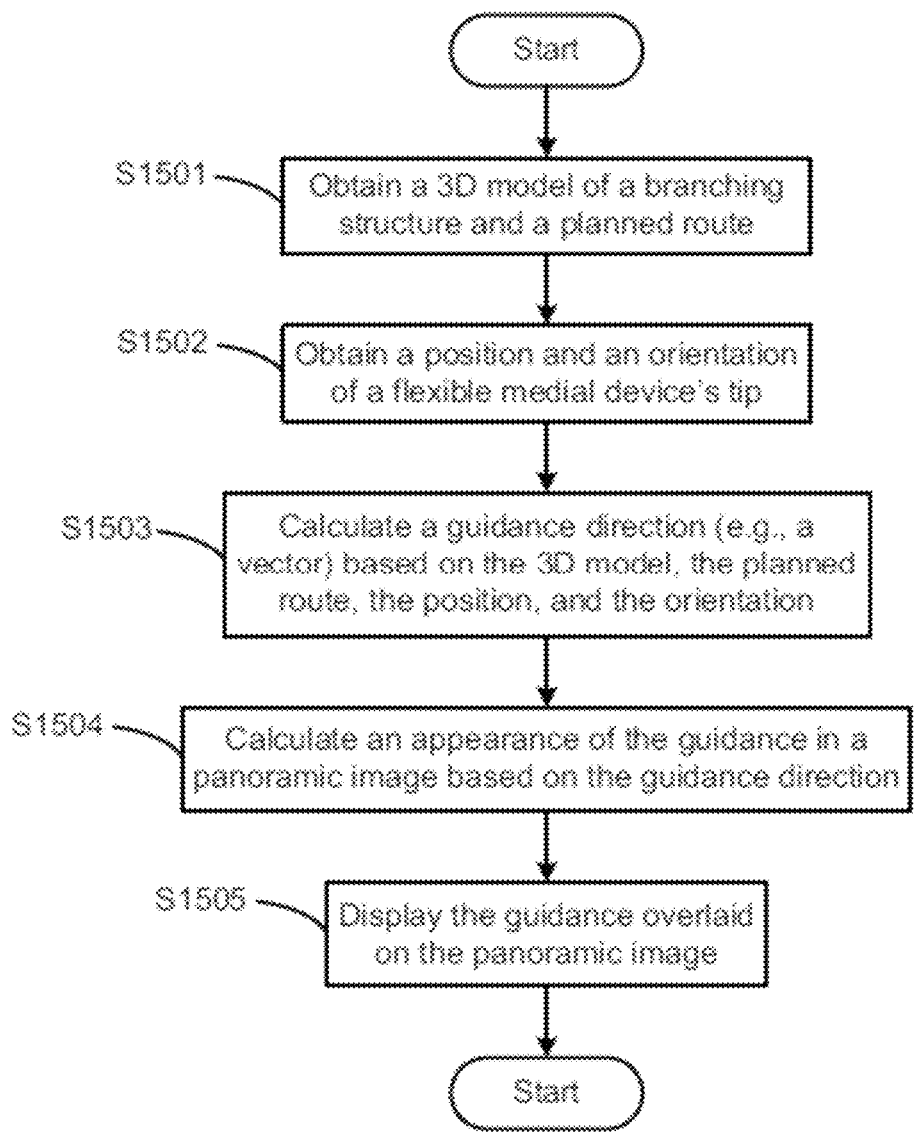
FIG. 14 illustrates an example embodiment of an operational flow for adding indicator guidance to a panoramic image.

FIG. 14 illustrates an example embodiment of an operational flow for adding guidance to a panoramic image. In S1501, a console obtains a 3D model of a branching structure and a planned route. In some embodiments, the console obtains the 3D model, the planned route, and a target. And, in some embodiments, the console obtains the 3D model and the target, but not the planned route.

Then, in S1502, the console obtains a position and an orientation (e.g., orientation vector) of a flexible medical device's tip. Next, in S1503, the console calculates a guidance direction (e.g., guidance vector) based on the 3D model, the planned route, the position, and the orientation. In some embodiments, the console calculates the guidance direction further based on the target. And, in some embodiments, the console calculates the guidance direction based on the 3D model, the target, the position, and the orientation, but not on the planned route.

In S1504, the console calculates an appearance of the guidance (e.g., the orientation of an arrow, the position of an arrow) in a panoramic image based on the guidance direction such that a direction indicated by the guidance in the panoramic image corresponds to the direction of the guidance in the 3D model. For example, the console may project the guidance vector onto a plane of the panoramic image.

Then, in S1505, the console causes the display to display the guidance overlaid on the panoramic image according to the appearance that was calculated in S1505.

Figure 15:
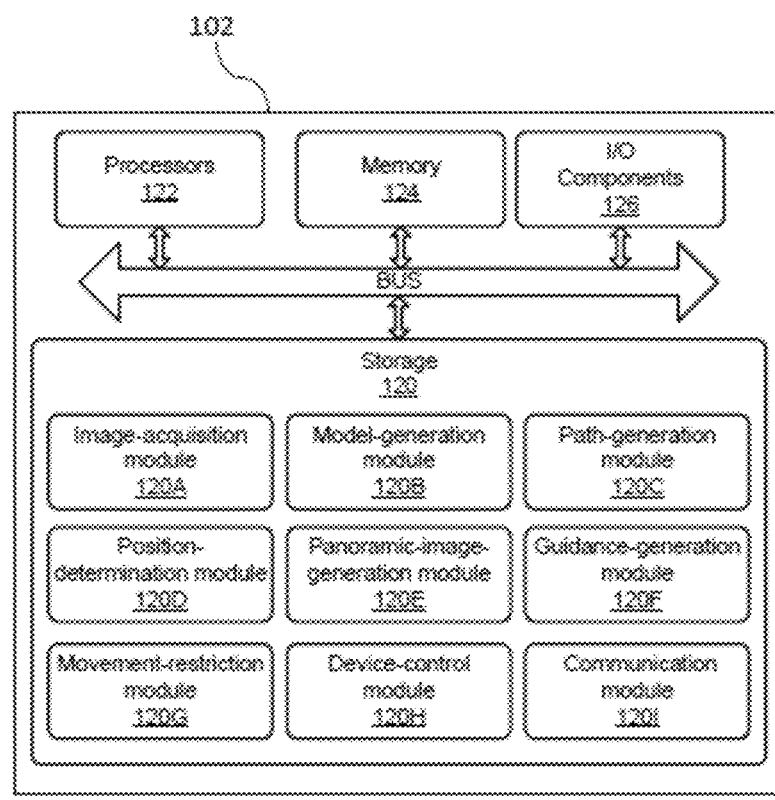
FIG. 15 illustrates an example embodiment of a console.

FIG. 15 illustrates an example embodiment of a console. The console 102 includes at least one storage 120, at least one processor 122, at least one memory 124, and one or more I/O components 126.

The console 102 additionally includes an image-acquisition module 120A, a model-generation module 120B, a path-generation module 120C, a position-determination module 120D, a panoramic-image-generation module 120E, a guidance-generation module 120F, a movement-restriction module 120G, a device-control module 120H, and a communication module 120I. A module includes logic, computer-readable data, or computer-executable instructions. In the embodiment shown in FIG. 15, the modules are implemented in software (e.g., Assembly, C, C++, C#, Java, BASIC, Perl, and Visual Basic). However, in some embodiments, the modules are implemented in hardware (e.g., customized circuitry) or, alternatively, a combination of software and hardware. When the modules are implemented, at least in part, in software, then the software can be stored in the storage 120. Also, in some embodiments, the console 102 includes additional or fewer modules, the modules are combined into fewer modules, or the modules are divided into more modules.

The image-acquisition module 120A includes instructions that cause the console 102 to acquire medial images, for example from an image capturing device, from another computing device (e.g., a server), or from external storage. For example, some embodiments of the image-acquisition module 120A include instructions that cause the console 102 to perform at least some of the operations that are described in S1101 in FIG. 5.

The model-generation module 120B includes instructions that cause the console 102 to generate a 3D model of a branching structure based on images (e.g., images in an image volume) of the branching structure. For example, some embodiments of the model-generation module 120B include instructions that cause the console 102 to perform at least some of the operations that are described in S1102 in FIG. 5.

The path-generation module 120C includes instructions that cause the console 102 to obtain a target (e.g., from a user input) in a 3D model of a branching structure and generate a path to the target through the 3D model. For example, some embodiments of the path-generation module 120C include instructions that cause the console 102 to perform at least some of the operations that are described in S1103 and S1104 in FIG. 5.

The position-determination module 120D includes instructions that cause the console 102 to perform a registration between an image space and a flexible-medical-device space and to determine (e.g., calculate) the position or orientation of a tip of a flexible medical device in a branching model. For example, some embodiments of the position-determination module 120D include instructions that cause the console 102 to perform at least some of the operations that are described in S102 in FIG. 6, in S1201 in FIG. 7, and in S1502 in FIG. 14.

The panoramic-image-generation module 120E includes instructions that cause the console 102 to generate and control the display of a panoramic image. For example, some embodiments of the panoramic-image-generation module 120E include instructions that cause the console 102 to perform at least some of the operations that are described in S104 and S105 in FIG. 6, in S1202 and S1203 in FIG. 7, in S1302 in FIG. 8, in S1401 and S1403 in FIG. 12.

The guidance-generation module 120F includes instructions that cause the console 102 to calculate a guidance direction and add guidance to a panoramic image. For example, some embodiments of the guidance-generation module 120F include instructions that cause the console 102 to perform at least some of the operations that are described in S1503, S1504, and S1505 in FIG. 14.

The movement-restriction module 120G includes instructions that cause the console 102 to restrict the movement of the flexible medical device. For example, some embodiments of the movement-restriction module 120G include instructions that cause the console 102 to perform at least some of the operations that are described in S1402 in FIG. 12.

The device-control module 120H includes instructions that cause the console 102 to control the movement of a flexible medical device. For example, some embodiments of the device-control module 120H include instructions that cause the console 102 to perform at least some of the operations that are described in S1404 and S1405 in FIG. 12.

The communication module 120I includes instructions that cause the console 102 to communicate with other devices (e.g., to acquire medical images, to store 3D models, to store routes). For example, some embodiments of the communication module 120I include instructions that cause the console 102 to perform at least some of the operations that are described in S1101 and S1105 in FIG. 5.

FIGS. 16(A)-16(C) illustrate movement patterns of a tip of a flexible medical device. In a first movement illustrated in FIG. 16(A), a first bendable portion (e.g., the distal section in FIG. 4) and the second bendable portion (e.g., the middle section in FIG. 4) are bent in the same direction. With this movement, the position and direction of the distal end of the flexible medical device can be changed by a large amount. Also, with this movement, the distal end of the flexible medical device can be swiveled through a large angular range. Also, in some embodiments, this movement can be achieved by moving the first bendable portion without moving the second bendable portion.

In a second movement illustrated in FIG. 16(B), the position of the distal end of the flexible medical device is moved while the angle thereof, that is, the viewing direction of the camera, is maintained constant. Therefore, this movement is suitable for, for example, moving an observation viewpoint along a wall surface. This movement allows a translational motion (e.g., an orthogonal translation motion along the viewing direction).

In a third movement illustrated in FIG. 16(C), the position and angle of the distal end of the flexible medical device are changed so that the line of sight of a camera constantly passes through a single distant point.

Thus, in some embodiments, after the registration of flexible medical device space and image space, the location of the flexible-medical-device's tip with respect to the branching model can be identified. Also, in some embodiments, along with the location information, the orientation of the flexible-medical-device's tip is used to synthesize the front view as well as swivel around desired rotation axis to generate the panoramic view.

In some embodiments, the three-dimensional branching model provides a resource to synthesize wide-angle view of the surrounding environment of the flexible-medical-device's tip. The pathway centerline and the orientation of the flexible-medical-device's tip provides a resource to draw the indication arrow to guide the flexible medical device towards the desired branch along the planned route.

In some embodiments, the panoramic image can show a panoramic view that was generated along a rotation axis of choice (e.g., yaw, pitch). A "fisheye" view can be offered by warping the swivel around all rotation axes between yaw and pitch.

In some embodiments, the panoramic image can be generated based on the vision in front of the flexible-medical-device's tip or can be generated at a viewpoint that is at a certain distance proximal from the tip to provide a perspective of the tip within the surroundings.

In some embodiments, the panoramic view can be provided, based on a user selection, to have a swivel with a desired rotation span.

And, in some embodiments, the panoramic view includes guidance (e.g., an arrow) that points to the direction for the operator to maneuver the flexible medical device towards the desired branch.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. A system comprising:
one or more memories; and
one or more processors in communication with the one or more memories, wherein the one or more processors operate with the one or more memories to cause the system to perform operations that include:
obtaining a model of a branching structure,
obtaining a position, relative to the branching structure, of a distal end of a flexible medical device,
obtaining at least one image of the branching structure from a camera at or near the distal end of the flexible medical device, and
generating a panoramic image of an interior of the branching structure at or near the distal end of the flexible medical device, wherein generating the panoramic image includes:
controlling the flexible medical device to move to a different orientation around yaw, pitch, or an oblique axis, or to a different lateral position,
capturing the at least one image of the branching structure at the different orientation or different lateral position, and
combining the at least one image with a one or more other images;
and wherein a field of view of the panoramic image is greater than a field of view of the camera.

2. The system of claim 1, wherein obtaining the at least one image of the branching structure, that are at or near the distal end of the flexible medical device includes:
generating the at least one image based on the model of the branching structure.

3. The system of claim 1, wherein controlling the camera to capture the at least one image includes controlling the camera, at the distal end of the flexible medical device, to rotate about a yaw axis, rotate about a pitch axis, or rotate about an oblique axis.

4. The system of claim 1, wherein the operations further include:
displaying at least part of the panoramic image on a display device.

5. The system of claim 4, wherein the operations further include:
restricting movement of the flexible medical device while the panoramic image is displayed on the display device.

6. The system of claim 4, wherein, part, but not all, of the panoramic image is displayed in the display device, and
wherein the operations further include changing the part of the panoramic image that is displayed on the display device in response to receiving an instruction.

7. The system of claim 4, wherein the operations further include:
receiving an indication of an orientation in the displayed at least part of the panoramic image; and controlling the flexible medical device to orient the distal end of the flexible medical device to the orientation.

8. The system of claim 1, wherein the operations further include:
obtaining a navigation route through the branching structure; and
adding a direction and/or guidance indicator to the panoramic image, wherein the direction and/or guidance indicator indicates a direction or a range of directions towards the navigation route.

9. The system of claim 1, wherein obtaining the position, relative to the branching structure, of the distal end of the flexible medical device comprises obtaining a position of a tracking sensor embedded at or near the distal end of the flexible medical device, and wherein combining the at least one image with the one or more other images comprising synthesizing a panoramic view image by stitching multiple view-angle images of an interior space of the model of the branching structure, based at a selectable distal position of the flexible medical device.

10. The system of claim 9, wherein a view angle of the panoramic view image spans at least −60° to +60°.

11. The system of claim 9, wherein the viewpoint is at a location proximal from the flexible medical device's tip and the panoramic view image shows a distal tip of the flexible medical device.

12. The system of claim 1, further comprising calculating a guidance direction range based on:
a) a next branch in the branching structure along a planned navigation route, or
b) the direction from the distal end of the flexible medical device to a target, and on the position of the distal end in relation to the branching structure, and on the orientation of the distal end, and
adding a guidance indicator, that indicates the guidance direction range, to panoramic image.

13. A method comprising:
obtaining a model of a branching structure;
obtaining a position, relative to the branching structure, of a distal end of a flexible medical device;
obtaining at least one image of the branching structure, that are at or near the distal end of the flexible medical device; and
generating a panoramic image of an interior of the branching structure at or near the distal end of the flexible medical device, wherein generating the panoramic image includes:
controlling the flexible medical device to move to a different orientation around yaw, pitch, or an oblique axis, or to a different lateral position,
capturing the at least one image of the branching structure at the different orientation or different lateral position, and
combining the at least one image with a one or more other images.

14. The method of claim 13, further comprising:
obtaining, from an input device, an instruction to change a view point of the at least one image of the interior of the branching structure; and
in response to obtaining the instruction, changing the view point of the at least one image of the interior of the branching structure.

15. The method of claim 14, further comprising:
obtaining, from the input device, an instruction to orient the flexible medical device in a selected orientation or combination of selected orientations; and
in response to obtaining the instruction, orienting the flexible medical device in the selected orientation or combination of selected orientations.

16. The method of claim 15, further comprising:
obtaining, from the input device, an instruction to move the flexible medical device; and
in response to obtaining the instruction to move the flexible medical device, moving the flexible medical device according to the instruction.

17. The method of claim 10, wherein generating the panoramic image includes stitching the at least one image.

18. The method of claim 13, wherein obtaining the at least one image of the branching structure, that are at or near the distal end of the flexible medical device includes:
obtaining the at least one image from an image volume.

19. The method of claim 13, further comprising displaying the panoramic image or displaying the panoramic image and at least one of the obtained at least one image of the branching structure.

20. The method of claim 13, further comprising:
obtaining a navigation route through the branching structure; and
adding a direction indicator to the panoramic image, wherein the direction indicator indicates a direction or a range of directions towards the navigation route.

21. One or more non-transitory computer-readable media storing instructions that, when executed by one or more computing devices, cause the one or more computing devices to perform the method of claim 13.

22. The one or more non-transitory computer-readable media of claim 21, wherein obtaining the at least one image of the branching structure, that are at or near the distal end of the flexible medical device includes:
obtaining the at least one image from an image volume.

23. The one or more non-transitory computer-readable media of claim 21, wherein obtaining the at least one image of the branching structure, that are at or near the distal end of the flexible medical device includes:
controlling the camera, at the distal end of the flexible medical device, to capture the at least one image, wherein the at least one image includes at least one second image that is captured at different orientation(s) of the camera.

* * * * *